United States Patent
Akiba

(10) Patent No.: US 6,422,995 B2
(45) Date of Patent: Jul. 23, 2002

(54) LINEAR TRANSMISSION MEMBER DRIVING UNIT FOR ENDOSCOPE

(75) Inventor: Haruo Akiba, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 90 days.

(21) Appl. No.: 09/725,749

(22) Filed: Nov. 30, 2000

(30) Foreign Application Priority Data

Dec. 3, 1999 (JP) .......................................... 11-344842
Mar. 21, 2000 (JP) ...................................... 2000-077876

(51) Int. Cl.$^7$ ................................................ A61B 1/06
(52) U.S. Cl. ...................................... 600/167; 600/168
(58) Field of Search ............................... 600/167, 168, 600/160

(56) References Cited

U.S. PATENT DOCUMENTS 6,059,721 A * 5/2000 Rudischhauser et al. .... 600/167
6,099,467 A * 8/2000 Kehr et al. ................... 600/167
6,117,071 A * 9/2000 Ito et al. ....................... 600/168

\* cited by examiner

*Primary Examiner*—Denise L. Esquivel
*Assistant Examiner*—Marc Norman
(74) *Attorney, Agent, or Firm*—Snider & Associates; Ronald R. Snider

(57) ABSTRACT

In the endoscope configured so as to drive a tip end portion movable lens for making the observation distance variable by the linear transmission member and to rotate this linear transmission member by a motor, a shaft of the motor is connected to a shaft connecting member, and a sliding guide hole having a predetermined length is formed on a cylindrical member wall of this shaft connecting member. And, within this shaft connecting member, a distal member of the linear transmission member is movably disposed, and this distal member is provided with a pin engaging with the sliding guide hole. This apparatus advances and retreats the linear transmission member in the rotating shaft direction during the bending operation, and provides a constant load to a motor rotating shaft, making it possible to obtain a stable magnification changing operation even though there may be a change in posture of an endoscope insertion unit. In addition, an outside diameter of the linear transmission member is formed to be smaller than a soft portion within an angle portion to reduce a frictional resistance during rotation.

10 Claims, 12 Drawing Sheets

31: SHAFT CONNECTNG MEMBER
34: SLIDING GUIDE HOLE
38: DISTAL MEMBER

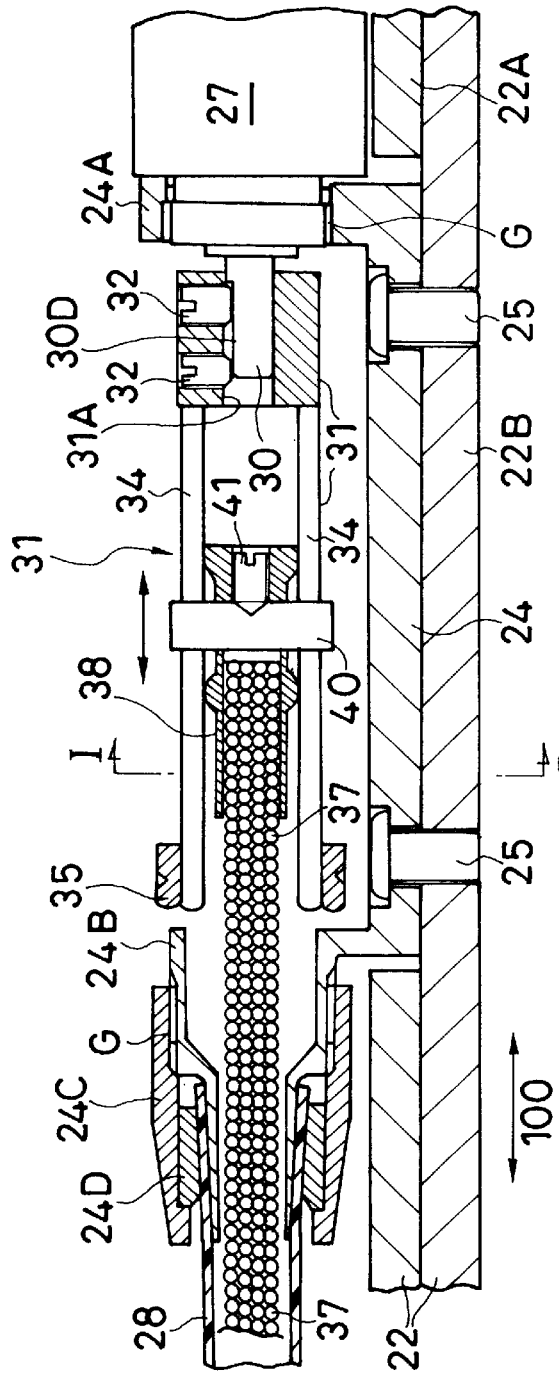
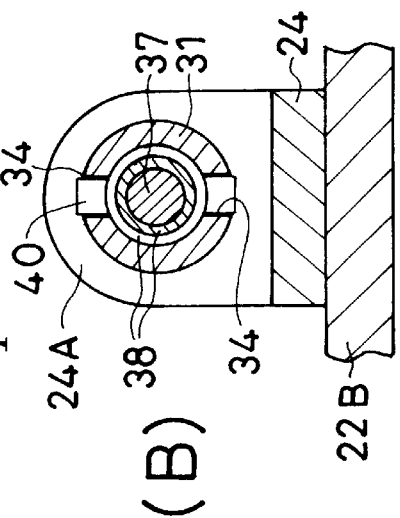
FIG.1(A)
FIG.1(B)
31: SHAFT CONNECTING MEMBER
34: SLIDING GUIDE HOLE
38: DISTAL MEMBER

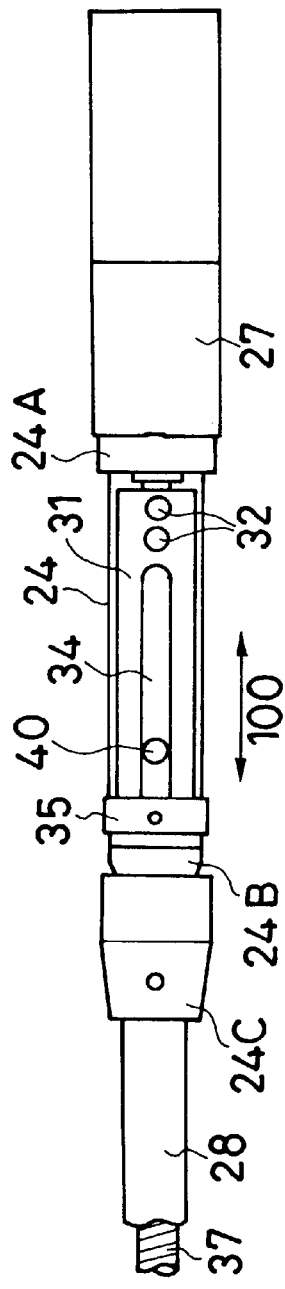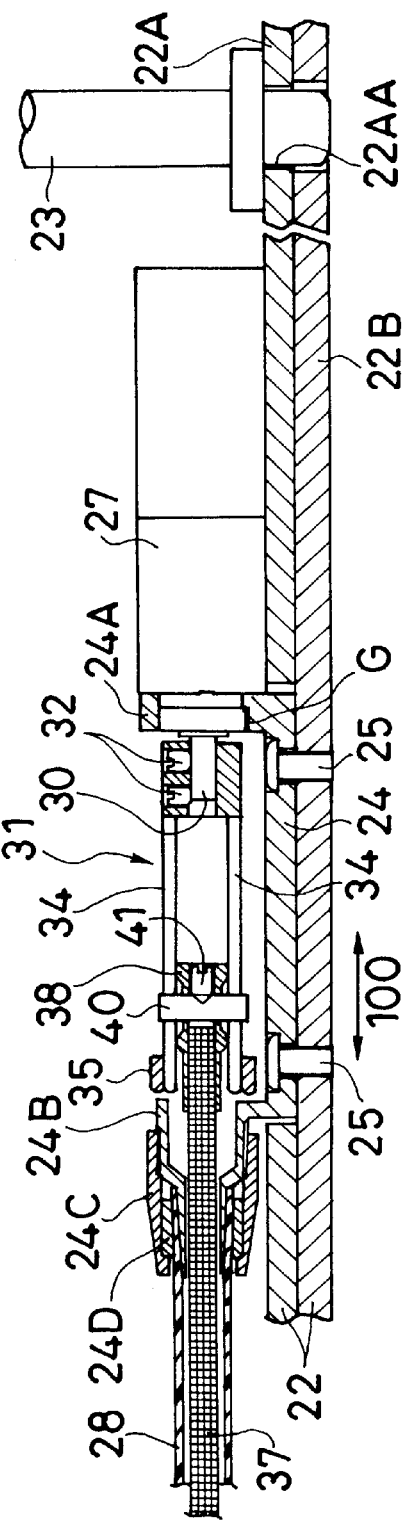

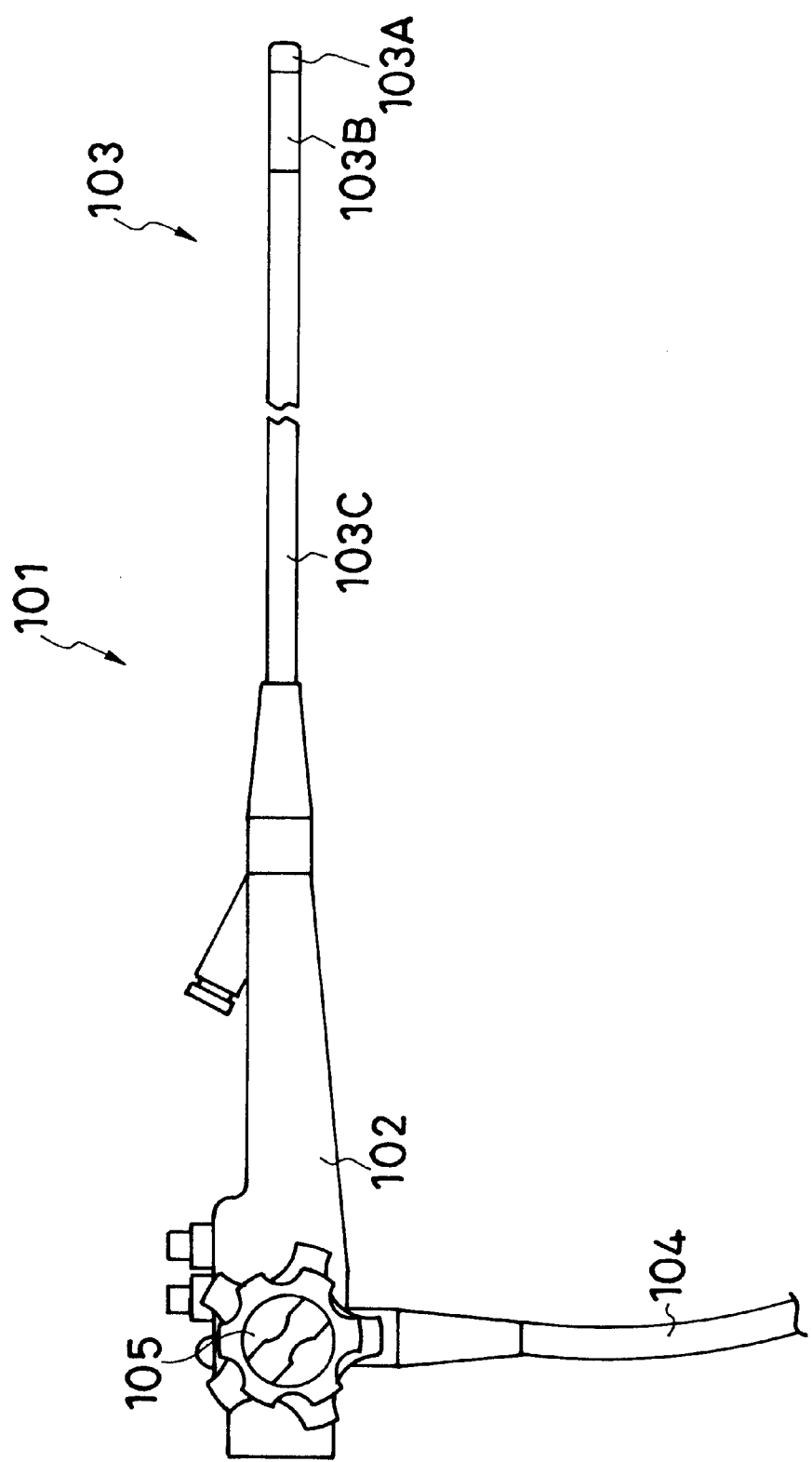

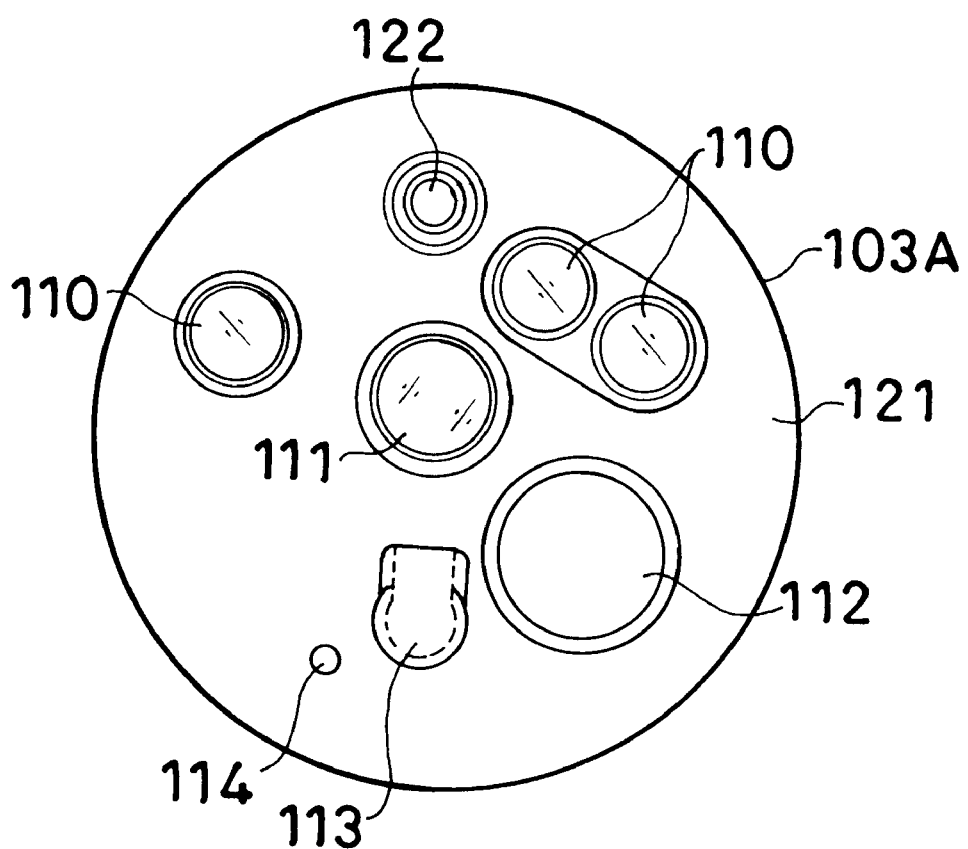

LINEAR TRANSMISSION MEMBER DRIVING UNIT FOR ENDOSCOPE

RELATED APPLICATIONS

This application claims the priority of Japanese Patent Application No. 11-344842 filed Dec. 3, 1999, and Japanese Patent Application No. 2000-77876 filed Mar. 21, 2000.

BACKGROUND OF THE INVENTION

1. Field of the Invention

The present invention relates to a linear transmission member driving unit for an endoscope, and more particularly to a driving unit for rotating a linear transmission member for changing an observation distance (including also changing depth of field) by a motor.

2. Description of the Prior Art

FIGS. 13A to 13C show a configuration of an endoscope (scope) to which a mechanism for making the observation distance (or depth of field) variable is applied, and FIG. 13A shows an endoscope operating unit 1A, and on the left side of this operating unit 1A, there are disposed an insertion unit 1B shown in FIG. 13B, and a tip end portion (hard portion) 1C shown in FIG. 13C. In this respect, the insertion unit 1B consists of the tip end portion 1C, an angle portion 1D and a soft portion 1E. Behind the operating unit 1A, there are disposed an air-supply/water-supply operating button 2A, a suction operating button 2B, a freeze switch 3A, other switches 3B and 3C, and an observation distance-variable switch 4 or the like.

Also, within the operating unit 1A, a motor 7 is mounted onto a chassis (base) 6 by a holding member 8, and a linear transmission member 10 formed of a multiple coiled spring is mounted to this motor 7 through a shaft connector 11. This linear transmission member 10 is placed within a flexible protective tube (soft tube) 12 in order to avoid any interference with other members, and this protective tube 12 is mounted to the chassis 6 with the holding member 13. These linear transmission member 10 and protective tube 12 are disposed from the operating unit 1A to the tip end portion 1C through the insertion unit 1B.

At the tip end portion 1C, there are disposed, as shown in FIG. 13C, an object lens 15, a movable lens 16 and a prism 17, and a CCD 18, which is a solid state imaging device, is optically connected below this prism 17. A holding member 19 of the movable lens 16 has a female threaded portion on top thereof, and on this female threaded portion, there is disposed a rotary driving member 20 whose male screwed portion threadably engages with this female threaded portion, and the linear transmission member 10 is coupled to the rotary driving member 20.

According to such a configuration, rotation of the motor 7 is transmitted to the rotary driving member 20 at the tip end portion 1C through the linear transmission member 10, and the rotary motion of this rotary driving member 20 is converted into a linear motion by means of threaded engagement with the holding member 19. This enables the movable lens 16 to move back and forth, making it possible to make an observation distance to be set in the objective optical system variable.

BRIEF SUMMARY OF THE INVENTION

Object of the Invention

In an endoscope having the above described linear transmission member driving unit, when an angle portion 1D of the insertion unit 1B is curved as shown in FIG. 13B, the protective tube 12 advances and retreats by a length of, for example, L1, and the linear transmission member 10 advances and retreats by a length of, for example, L2 in a rotating shaft direction. More specifically, on focusing attention on a certain point P on the protective tube 12, it moves forward (toward a position P1) by a length L1 when the angle portion 1D is bent from a straight state. Since both end portions of the protective tube 12 are fixed to the neighborhood of its tip end portion 1C and the holding member 13, when the insertion unit 1B is set to a just suitable length in a straight state, the protective tube 12 is pulled during the bending operation, and as a result, the tip end portion 1C is deviated from a desired operating direction and tilts, so-called "crooked neck" occurs. Thus, conventionally, the length of the protective tube 12 has been made a little longer than the armored body, and when it is being bent, the scope insertion unit 1B is disposed so as to push it into the protective tube 12.

On the other hand, one end of the linear transmission member 10 is connected to the rotary driving member 20, and is enveloped in the protective tube 12, and therefore, when the angle 1D is bent, the linear transmission member 10 moves backward (from position P to P2) by, for example, length L2. For this reason, there occurs an inconvenience that the linear transmission member 10 gives a load caused by pressure to the output shaft of the motor 7, and a change in posture of the insertion unit 1B changes the moving speed of the movable lens 16, that is, the magnification changing time. Thus, the linear transmission member 10 is mounted with reference to the time during the bending operation of the insertion unit 1B (during the maximum movement toward the motor side), and when the insertion unit 1B is made straight, a moderate pulling force is caused by a multiple coiled spring (linear transmission member 10) which expands and contracts so as to cause any load of the pressure not to be applied to the motor output shaft.

Since, however, the degree of expansion and contraction of the multiple coiled spring, which is the linear transmission member 10, changes depending upon bending (change in posture) of the insertion unit 1B including the angle portion 1D even in the above described configuration, the load to the motor output shaft cannot be maintained constant, leading to a problem that the posture of the insertion unit 1B causes variations in the magnification changing operation (operation of variable power).

Also, the angle portion 1D configuring the endoscope is used to point a tip hard portion 1C toward a desired direction, and is constructed so as to be curved by remote control from an angle operating device provided on the body operating unit 1A. This angle portion 1D is curved in order to mainly change the observation visual field of the endoscope. The insertion unit 1B is inserted into a narrow body cavity in order to perform inspection and diagnosis, and the overall length of the angle portion 1D is desirably made as short as possible in order to smoothly and reliably change the observation visual field even in the narrow body cavity or the like. Moreover, in order not to cause any dead angle in the observation visual field as far as possible, the angle of curvature must be made as large as possible. Accordingly, when the angle portion 1D is curved to the maximum angle of curvature, the radius of curvature is exceedingly small, and yet it is configured to be able to be abruptly curved such as, for example, 180° or an angle of its vicinity. Also, since an insertion course within the body cavity has a complicatedly curved shape, the soft portion 1E coupled to the angle portion 1D has flexibility in a curved direction, and this soft portion is constructed so as to be able to be curved in any direction by following the curved insertion course.

The angle portion 1D is constructed so as to be curved larger than the soft portion 1E, and even in the protective tube 12 to be disposed within these, the inside of the angle portion 1D is curved larger so that the soft protective tube 12 becomes deformed as if it were crushed. Therefore, within this angle portion 1D, the frictional resistance of the linear transmission member 10 and the protective tube 12 becomes larger than the soft portion 1E, resulting in irregularity of the rotary driving-force of the linear transmission member 10, and there is a problem that the driving force lowers.

Further, in a state in which the angle portion 1D has been curved to the maximum, the protective tube 12 may become deformed so as to become flat, but since the linear transmission member on the one hand has high rigidity, and a change in the sectional shape is small, the linear transmission member 10 goes into a state in which the linear transmission member 10 is pressed into contact with the protective tube 12. Thus, when the linear transmission member 10 is caused to be rotated in this state, there is a problem that the frictional resistance due to rotation becomes large, resulting in a greater motor load.

The present invention has been achieved in the light of the above described problems, and is aimed to provide a linear transmission member driving unit for an endoscope capable of improving the transmission efficiency of a rotary driving force of the linear transmission member, reducing the load onto the motor, and maintaining operations such as magnification changing constant even if there may be a change in the posture of the endoscope insertion unit.

SUMMARY OF THE INVENTION

In order to attain the above described object, a linear transmission member driving unit for an endoscope according to the present invention is provided with: a linear transmission member which performs a rotary motion in order to drive an object; a protective tube which rotationally envelops this linear transmission member; a motor, to which the linear transmission member is shaft-connected; a chassis to which this motor is fixed; and a mobile type linear transmission member shaft coupling mechanism, which couples the shaft of the motor fixed to this chassis to an end portion of the linear transmission member, and to which this linear transmission member is mounted so as to be able to move in a direction of the rotating shaft of the motor.

The mobile type linear transmission member shaft coupling mechanism consists of a cylindrical member coupled and fixed to the motor shaft, and comprises: a shaft connecting member in which a sliding guide hole having a predetermined length in the direction of the rotating shaft is formed; and a distal member of the linear transmission member, which is disposed so as to move within a cylinder of this shaft connecting member, and, in which there is provided a pin for engaging with the sliding guide hole to slide, and a pin of this distal member is caused to be engaged with the sliding guide hole, whereby it is made possible to transmit rotation of the motor to the linear transmission member and to move the linear transmission member concerned in the direction of the rotating shaft by a predetermined amount.

According to the above described invention, it becomes possible for the distal member of the linear transmission member to move in the direction of the rotating shaft by the length of the sliding guide hole within the cylinder of the shaft connecting member, and this linear transmission member advances or retreats in the direction of the rotating shaft in response to the angle bending operation, and therefore, the linear transmission member consisting of a multiple coiled spring or the like does not expand nor contract any longer (even if it expands or contracts, its degree becomes small), but the load to be applied to the motor rotating shaft becomes substantially constant. Therefore, even if the insertion unit changes its posture, the magnification changing operation or the like can be executed by the stable rotary driving force.

In addition, the motor and the mobile type linear transmission member shaft coupling mechanism are disposed in space on the side of an angle operating knob mechanism being mounted, partitioned by the chassis within an operating unit, and the motor and the protective tube can be mounted to the chassis concerned by the use of an integrally formed holding member. Thereby, the space can be efficiently utilized, and any interference of the motor and the mobile type linear transmission member shaft coupling mechanism with various contents within the operating unit can be avoided. In other words, within the displacement space at a side opposite to the angle operating knob mechanism partitioned by the central chassis within the operating unit, there are disposed contents such as various conduit lines, light guides, and signal lines, and if the driving mechanism were disposed here, there would be such inconvenience that damage or the like to the contents occurs due to the interference. Thus, the influence on such contents can be avoided. Also, it becomes easy to position such that the motor driving shaft coincides with the central position of the protective tube.

Further, if as the above described chassis, a plurality of sheets of plates are superposedly disposed, it will be possible to mount the rotating shaft for the angle operating knob and the holding member onto different plates respectively, and in this case, there is an advantage that it becomes difficult for vibration during rotation of the motor to transmit to the angle operating knob.

It is preferable to apply lubricating coat to the sliding member of the mobile type shaft coupling mechanism, and in this case, it is capable of securing a smooth sliding operation by the lubricating coat, and improving the abrasion resistance.

On the outer periphery of the distal member, there are formed protruding portions in contact with the inner wall of the shaft connecting member at two positions where the pin is sandwiched therebetween such that the linear transmission member can be moved by sliding of these protruding portions within the shaft connecting member concerned. Thereby, it is possible to realize a smooth moving operation of the linear transmission member without the distal member tilting from the motor shaft direction (while maintaining parallelism) even though a force for tilting (falling) in a direction perpendicular to the moving direction may be exerted on the linear transmission member and the distal member.

A linear transmission member driving unit for an endoscope according to another invention is provided with: a movable member disposed on the side of the tip end of an insertion unit having an angle portion and a soft portion; a transmission coil comprising wire spirally wound, which is a linear transmission member for transmitting the rotary driving force of the motor to this movable member; and a flexible protective tube which rotationally envelops this transmission coil. The transmission coil, whose wire diameters are actually the same, consists of two coil portions having different outside diameters, and has a small-diameter coil portion having smaller outside diameter within the angle portion, and a large-diameter coil portion having larger outside diameter within the soft portion. These both coil portions are coupled by a coupling member so as to be able to integrally rotate at a connecting position between the angle portion and the soft portion or in the vicinity thereof.

The outside diameter of the small-diameter coil portion is preferably set so as to be smaller than the size in the direction of the end shaft when the angle portion goes into a maximum curved state and the protective tube becomes deformed so as to be flattened. According to this another invention, it becomes possible to efficiently transmit the rotary driving force by reducing the frictional resistance.

BRIEF DESCRIPTION OF THE DRAWINGS

FIG. 1A shows a linear transmission member driving unit for an endoscope according to a first embodiment of the present invention, and is a side view obtained by enlarging a portion of the mobile type linear transmission member shaft coupling mechanism of FIG. 2B;

FIG. 1B is a sectional view taken on a line I—I in FIG. 1A;

FIG. 2A is a top view showing a linear transmission member for an endoscope according to the first embodiment;

FIG. 2B is a side view showing the sectional view of one portion of FIG. 2A;

FIG. 5 is a schematic structural view showing an endoscope according to a second embodiment of the present invention;

FIG. 6 is an external view showing a tip end surface of the insertion unit of the endoscope of FIG. 5;

DETAILED DESCRIPTION OF THE PREFERRED EMBODIMENTS

First Embodiment

Figure 3A:
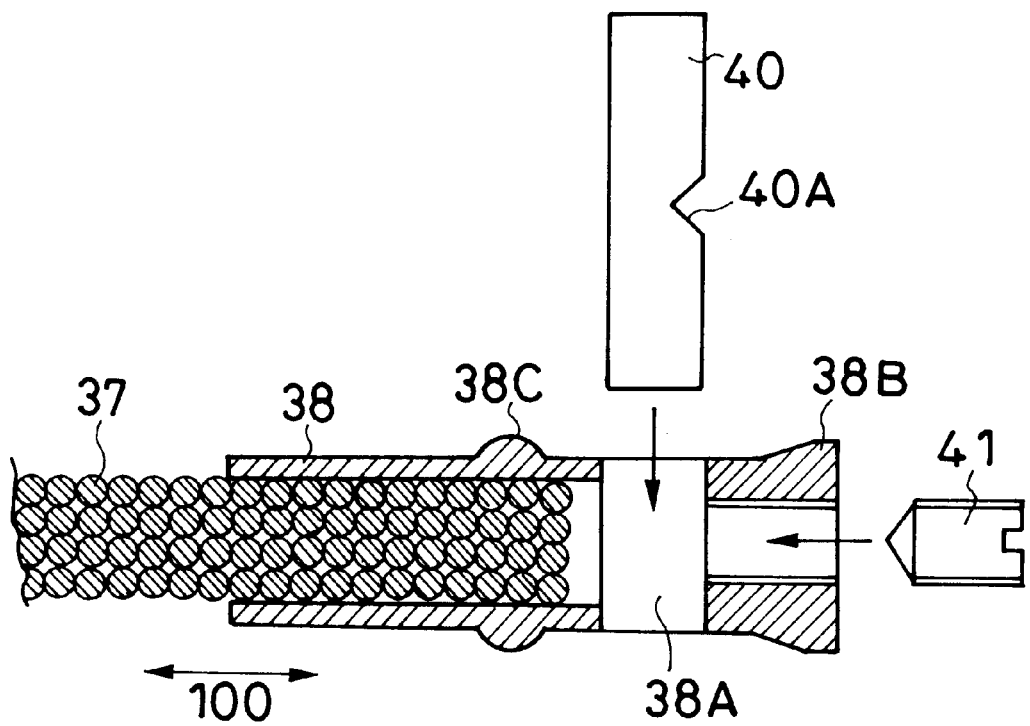
FIG. 3A is an exploded view showing a distal member of the linear transmission member according to the first embodiment.

FIGS. 1 to 3 show a linear transmission member driving unit for an endoscope (motor-side driving unit to be disposed in the endoscope operating unit) according to a first embodiment, and FIG. 1A is an enlarged view showing the shaft coupling mechanism of FIG. 2B. In FIGS. 1 and 2, a chassis 22 comprises two sheets of plates superimposed, is disposed at the center within the operating unit, and the supporting shaft 23 of an angle operating knob is fitted in and fixed to an upper side plate 22A of this chassis 22 [FIG. 2B]. Although detail of this fixation is not shown, the lower portion of the supporting shaft 23 is fitted into a mounting hole 22AA of the upper side plate 22A, and the supporting member of the angle operating knob is fixed to the upper side plate 22A by a screw. This angle operating knob curves the angle portion and the tip portion through wire by rotation of a left-right angle operating knob (45A) and an upper-lower angle operating knob (45B) to be described later in FIG. 4.

A holding member 24 for the motor and the protective tube is mounted to the lower side plate 22B of the chassis 22 by means of two screws 25. More specifically, the holding member 24 of the motor-side driving unit is mounted to a lower side plate 22B, which is different from the upper side plate 22A, on which the supporting shaft 23 of the angle operating knob has been mounted, whereby vibration or the like during the motor driving are prevented from transmitting to the angle operating knob side. Also, since the entire driving unit shifts downward, space within the operating unit can be effectively utilized in order to dispose other members.

In this holding member 24, a tip screw portion G of the motor 27 is threadably engaged with, and is fixed to a threaded portion G within an annular portion 24A in the rear holding portion and the protective tube 28 is held and fixed by means of combined cylindrical portions 24B to 24D in the front holding portion. More specifically, the screw portion G for threadably engaging with a contact surface between the cylindrical portions 24B and 24C is formed, and an outer periphery on the side of tip end of this cylindrical portion 24B and an inner circumference of the cylindrical portion 24D are made into a tapered surface respectively, and between these tapered surfaces, there is provided space for sandwiching the protective tube 28 therebetween. Therefore, the cylindrical member 24C is threadably engaged with and coupled with the cylindrical portion 24B in a state in which the protective tube 28 is sandwiched between the cylindrical portions 24B and 24D, thereby the protective tube 28 can be reliably held and fixed.

On the other hand, the shaft 30 of the motor 27 is mounted to the shaft connecting member 31. More specifically, the shaft 30 is inserted into the mounting hole 31A of this shaft connecting member 31, and a D-cut surface of this shaft 30 is fastened by two screws 32, whereby the motor shaft 30 is fixed to the shaft connecting member 31. This shaft connecting member 31 has a cylindrical member as the main body, and has a sliding guide hole 34 formed along the rotating shaft direction 100 at two places (may be one place or the like) which, for example, oppose to each other on the wall of the cylindrical member, and a stopper ring 35 is mounted to its tip end with adhesive. The length of this sliding guide hole 34 is set to be slightly longer than a spring displacement (movement in the rotating shaft direction 100)

of the linear transmission member 37 when the angle portion has been curved.

The end portion of the linear transmission member 37 consisting of a multiple coiled spring or the like disposed within the protective tube 28 is inserted into the distal member (for example, sleeve) 38 and fixed by soldering or the like, this distal member 38 is constructed so as to slide within the cylindrical member of this shaft connecting member 31, and the pin 40 is mounted with a screw 41. FIG. 3 shows a state before the pin 40 is mounted, and the distal member 38 shown is formed with a mounting hole 38A in a direction perpendicular to the rotating shaft direction 100, the pin 40 is inserted into this mounting hole 38A, and a sharp point of the screw 41 is screwed in so as to apply to a concave portion 40A in the pin 40, whereby the pin 40 is mounted to the distal member 38.

As shown in FIG. 3A, annular projections 38B and 38C are formed at two places before and after a pin mounting hole 38A on the outer periphery of the distal member 38 concerned so as for the distal member 38 to be able to smoothly slide without tilting and with reduced frictional resistance within the shaft connecting member 31. Further, lubricating plating is applied to the surfaces of movable members such as the shaft connecting member 31, the distal member 38 and the pin 40. More specifically, the above described movable members are made of stainless steel, and their surfaces will be coated with lubricating plating using plating liquid containing Teflone (trade name). This coating provides excellent abrasion resistance and slip properties to the movable portions.

Figure 3B:
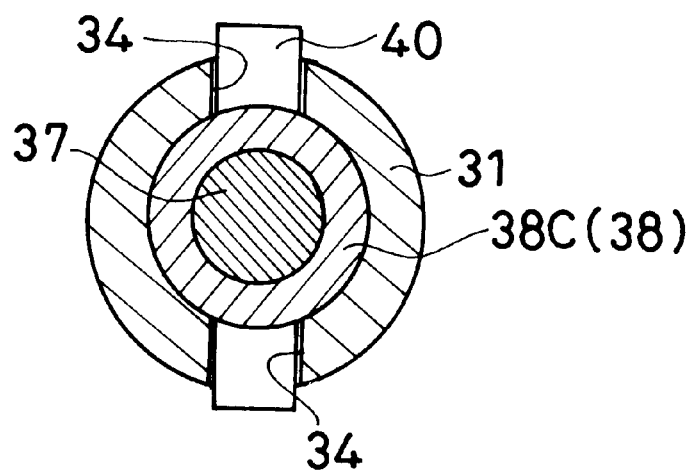
FIG. 3B is a sectional view showing a portion obtained by cutting off the distal member of the annular protruding portion of the linear transmission member (including a shaft connecting member)

As shown in FIG. 3B, in the engagement between the sliding guide hole 34 and the pin 40 in the shaft connecting member 31, the width of the shaft connecting member 31 and the outside diameter of the pin 40 are set to dimensions to cause no play in the rotating direction to such a degree that the sliding is not prevented. This setting enables the response on transmitting the rotation of the motor 27 to the linear transmission member 37 to be made excellent.

In the mobile type linear transmission member shaft coupling mechanism using such a shaft connecting member 31, the distal member 38 moves in the rotating shaft direction 100 within the shaft connecting member 31 within a range in which the pin 40 slides within the sliding guide hole 34, and the engagement between the sliding guide hole 34 and the pin 40 causes the linear transmission member 37 and the distal member 38 to be fixed to the shaft connecting member 31 in the rotating direction, and the rotation of the motor 27 is transmitted to the linear transmission member 37 through the motor shaft 30 and the shaft connecting member 31.

Figure 4A:
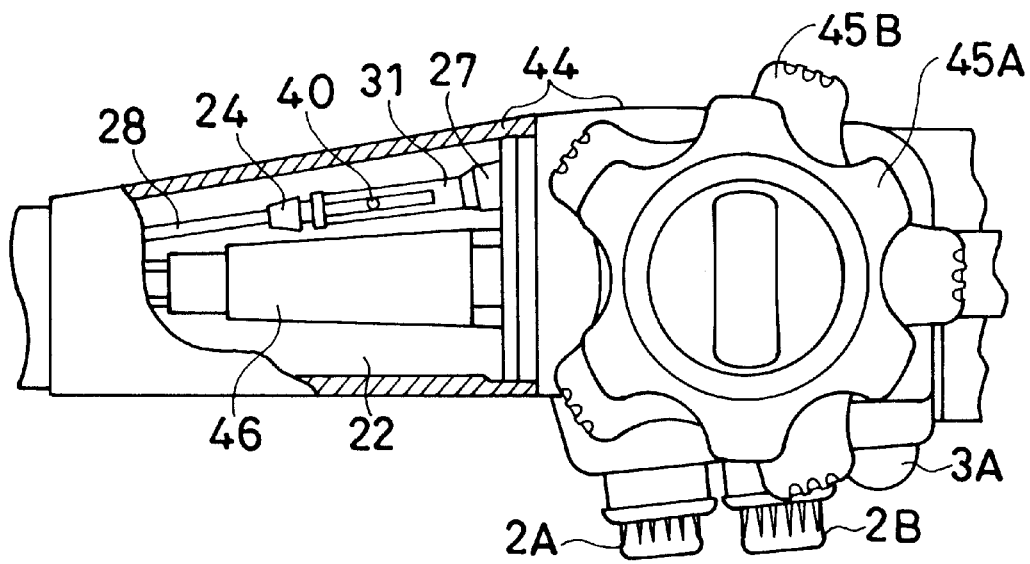
FIG. 4A is a view showing layout of each member on the side on which the angle operating knob mechanism has been disposed in the operating unit according to the first embodiment.
Figure 4B:
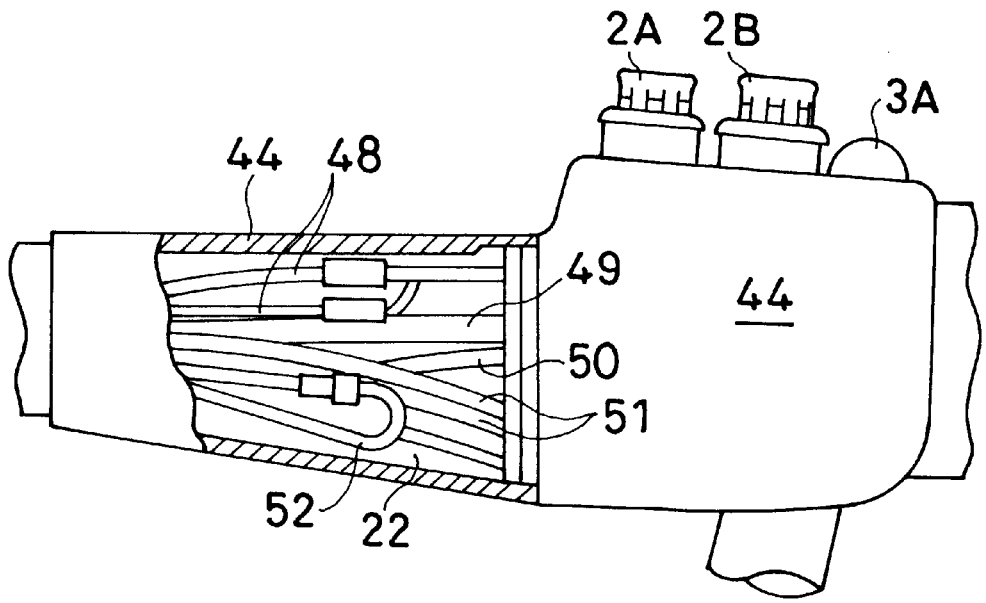
FIG. 4B is a view showing the side on which various conduit lines, signal cable or the like are disposed, on the opposite side to the operating unit of FIG. 4A.

FIGS. 4A and 4B show the disposition of each member in the endoscope operating unit, and in an operating unit 44, there are, as shown, disposed a left-right angle operating knob (rotational member) 45A and an upper-lower angle operating knob 45B together with an air-supply and water-supply operating button 2A, a suction operating button 2B, a freeze switch 3A. The interior of the operating unit 44 is divided into two spaces by a chassis 22 mounted at the central portion, and as shown in FIG. 4A, in the space in which the angle operating knob mechanism is disposed, an angle wire sliding portion 46 is mounted to the chassis 22, and together with the angle wire sliding portion 46, there are provided a motor 27, which is the mobile type linear transmission member shaft coupling mechanism, a shaft connecting member 31, the protective tube 28 which envelops the linear transmission member 37, or the like.

On the other hand, as shown in FIG. 4B, in the opposite-side space to this operating unit 44, there are provided an air supply/water-supply tube 48, a suction tube 49, signal cable 50, a light guide bundle 51, a water jet tube 52 or the like. Such disposition effectively utilizes the space within the operating unit 44, and prevents the mobile type linear transmission member shaft coupling mechanism from exerting influences such as vibration upon other members.

The first embodiment has the above described configuration, and as described above, the protective tube 28 is surely fixed to the chassis 22 by the holding member 24 with a predetermined amount to be pushed in. More specifically, when curving the insertion unit (1B) including the angle portion (1D), the protective tube 28 is pushed in and is disposed allowing for room, whereby when this insertion unit is made straight, the protective tube 28 can be prevented from being crushed by being pulled. On the other hand, the linear transmission member 37 can be movably mounted in the rotating shaft direction 100 by means of the mobile type shaft coupling mechanism of the distal member 38 and the shaft connecting member 31. Therefore, when the angle portion is curved by the angle operating knobs 45A and 45B, the linear transmission member 37 is to move in the rotating shaft direction 100.

FIG. 2B shows a state in which the linear transmission member 37 and the distal member 38 have moved a little from the positions of FIG. 1A, and when the angle portion, which has been, for example, curved, is returned straight, the linear transmission member 37 is pulled so that the distal member 38 thereof moves forward (the left side of the figure) within the shaft connecting member 31 as shown. Conversely, when it is curved, the distal member 38 of the linear transmission member 37 moves backward (right side of the figure).

As described above, the linear transmission member 37 moves in the rotating shaft direction 100 in response to the angle portion curving operation or the curving of the insertion unit (change in posture), and therefore, it will not rotate in an expanded state, but even if it may expand or contract, the amount of expansion or contraction becomes small. Therefore, the load to be applied to the motor shaft 30 becomes substantially constant, and stable magnification changing operation is performed irrespective of the change in posture of the scope insertion unit.

The movement operation of the distal member 38 within the shaft connecting member 31 is smoothly performed without rattling by means of the lubricating plating and the existence of annular projections 38B and 38C at two places. Further, since the holding member 24 for the motor 27 and the protective tube 28 has been mounted to a chassis plate (22B), which is different from a chassis plate (22A), to which the supporting shaft 23 for the angle operating knob has been fixed, it becomes difficult for vibration caused by driving of the motor 27 and vibration caused by the rotation of the linear transmission member 37 to transmit to the angle operating knob, and there is an advantage that the operation is caused not to perceive those vibrations.

As described above, according to the first embodiment, the linear transmission member advances or retreats in the rotating shaft direction in response to the angle curving operation, and will not advance or retreat and yet the load onto the motor shaft becomes constant. Therefore, even if there maybe a change in posture of the insertion unit of the endoscope, stable operation, for example, magnification changing speed or the like can be obtained.

In addition, effective utilization of the space within the operating unit improves the assembly property, and enables any interference of the motor and the mobile type linear transmission member shaft coupling mechanism with various contents within the operating unit to be avoided. Also, since the motor and the protective tube have been mounted to the integrally formed holding member, it becomes easy to position so as to cause the driving shaft of the motor to coincide with the center position of the protective tube.

Further, since if as the chassis, a plurality of plates are superposedly disposed, and the rotating shaft for the angle operating knob and the holding member for the motor-side driving portion have been mounted onto different plates respectively, there is an advantage that it becomes difficult for vibration during rotation of the motor to transmit to the angle operating knob.

Also, a smooth sliding operation can be secured by the lubricating coat, the abrasion resistance is also improved, and even when a force for tilting in a direction perpendicular to the moving direction is exerted on the linear transmission member and the distal member, the distal member does not tilt from the motor shaft direction, but the linear transmission member can be smoothly moved.

Second Embodiment

Next, with reference to FIGS. 5 to 12, the description will be made of the configuration of a second embodiment according to the present invention.

First, FIG. 5 shows the schematic configuration of the entire endoscope. As seen from FIG. 5, the endoscope 101 is generally constructed by providing the insertion unit 103 for the body cavity or the like contiguous to the body operating unit 102, and drawing a universal cord 104 from the body operating unit 102. The insertion unit 103 provided contiguous to the body operating unit 102 is divided into a tip hard portion 103A, an angle portion 103B and a soft portion 103C in order from the tip end side in terms of the function and structure.

The tip hard portion 103A is made of a hard member, and on its tip end surface, there are, as shown in FIG. 6, provided an illumination portion 110, an observation portion 111, a treatment tool guiding portion 112 and a washing nozzle 113. Further, a jet water-supply portion 114 is opened. The angle portion 103B is configured such that the tip hard portion 103A provided with the observation portion 111 can be curved in various directions such as up and down, and left and right by means of an angle knob 105 provided on the body operating unit 102 in order to turn the tip hard portion 103A in a desired direction. Further, the soft portion 103C accounts for the greater part of the length of the insertion unit 103, has flexibility in the curving direction, and is constructed to have resistance to collapse, and therefore, it can be bent in any direction along the insertion course.

Figure 7:
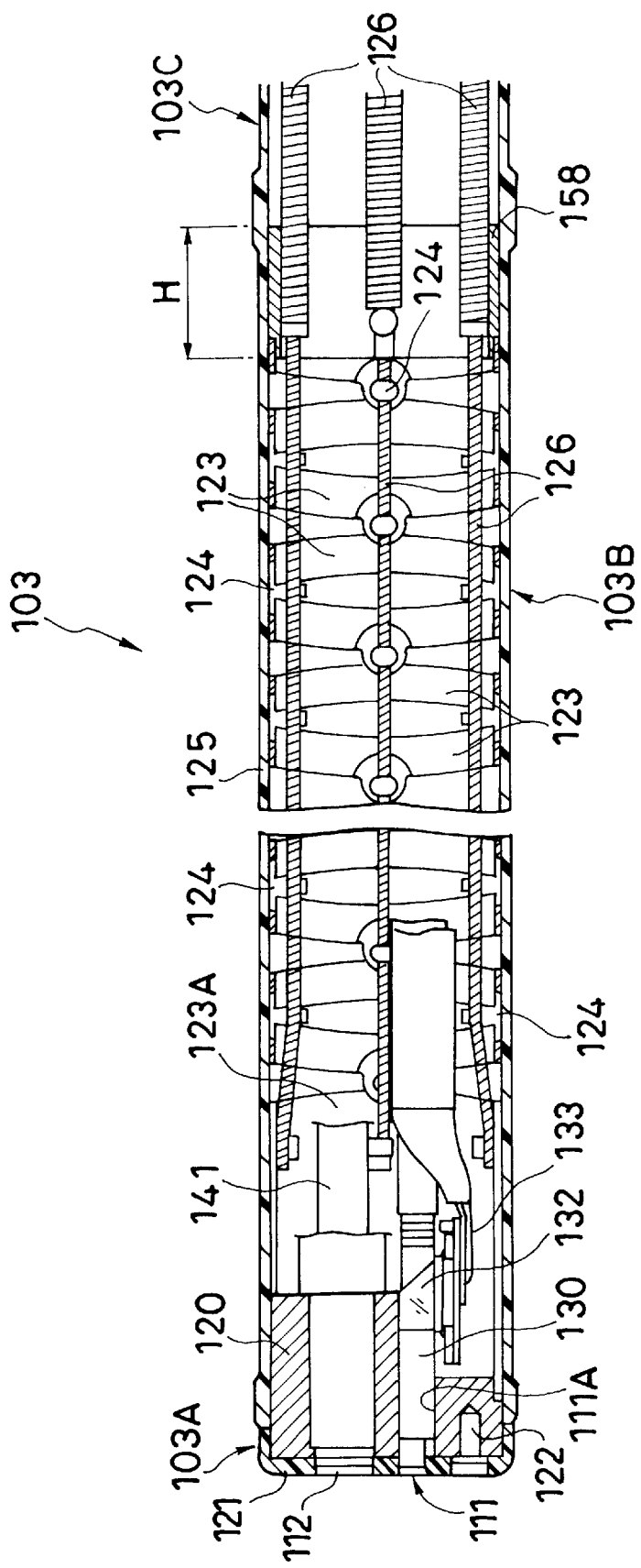
FIG. 7 is a longitudinal sectional view showing the vicinity of the tip end of the insertion unit.

FIG. 7 shows a section for a portion of the insertion unit 103 on the tip end side. As apparent from this drawing, the tip hard portion 103A has a body block 120 made of, for example, metal, and this body block 120 is formed with through holes which penetrate in the axial direction at needed places. On the tip end surface of the body block 120, there is mounted an insulating cap 121, which is fixed to the body block 120 with a set screw 122. The angle portion 103B has a ring joint structure in which a multiplicity of angle rings 123 are successively pivotally mounted by means of pivot pins 124, and on the outer periphery of the ring joint structure consisting of angle rings 123, there is provided a covering member 125 including a metallic net and an external layer consisting of fluororubber, EPDM, urethane rubber or the like. Further, four pieces of operating wires 126 are extended from the interior of the angle portion 103B toward the soft portion 103C, and these operating wires 126 make a pair of upper and lower ones, and of left and right ones respectively. When one of the pair of upper and lower operating wires is pulled, and the other is let out, the angle portion 103B is curved in the up-and-down direction, while when one of the pair of left and right operating wires is pulled, and the other is let out, the angle portion 103B is curved in the right-and-left direction.

The angle portion 103B is curved up or down, left or right, but the angle portion 103B is curved in this manner in order to turn the tip hard portion 103A in a desired direction. Thereby, the tip hard portion 103A of the insertion unit 103 can be turned in the desired direction within the insertion course, which is curved or branches. Also, when the insertion unit 103 has been disposed at a position to perform observation or diagnosis within a body cavity, the angle portion 103B is also curved on changing the direction of the observation visual field. As regards the degree of curvature when the angle is being operated in order to change the observation direction, it is curved at a very large angle of curvature such as 108° or more as the maximum curved angle. And yet since the angle is curved to the maximum angle of curvature within the narrow body cavity, the length dimension of the angle portion 103B is made very short as compared with the full length of the soft portion 103C, and therefore, the angle portion 103B is to be abruptly curved in the maximum angle of curvature state.

Of a multiplicity of angle rings 123 coupled with one another constituting the angle portion 103B, a tip ring 123A located at the extreme tip is coupled to the body block 120. Therefore, in the insertion unit 103, a portion between the tip surface of the insulating cap 121 and the tip ring 123A of the angle portion 103B, and a pivotally-mounted portion with another angle ring 123 to be pivotally mounted thereon is the hard portion.

Figure 8:
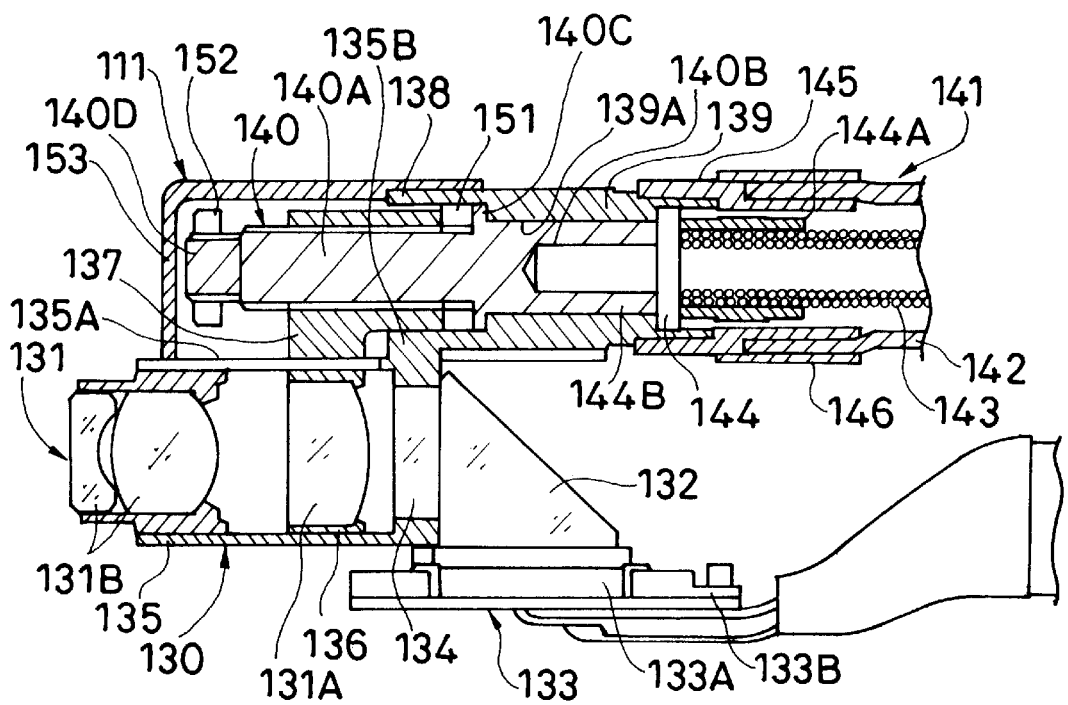
FIG. 8 is a longitudinal sectional view showing a driving mechanism for a movable lens of an observation portion.
Figure 9:
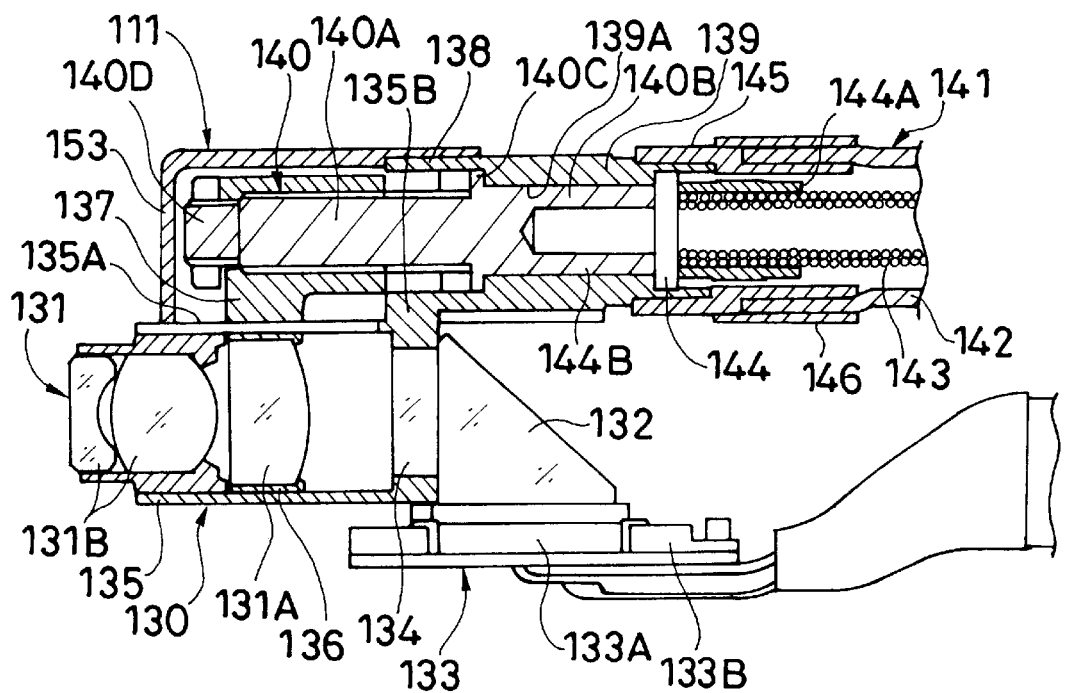
FIG. 9 is a sectional view similar to FIG. 8, showing a state in which the movable lens has been advanced.

As regards the configuration of the observation portion 111 provided at the tip end portion of the tip hard portion 103A, the description will be made with reference to FIGS. 8 to 10. In these figures, reference numeral 130 denotes a lens assembly constituting an objective optical system provided in an observation portion mounting portion 111A (See FIG. 7) provided in the body block 120, and this lens assembly 130 has an object lens group 131, and an optical path from this object lens group 131 is to be bent with 90° turned downward by means of a prism 132. At an image focusing position of the object lens group 131, there is disposed a solid state imaging device assembly 133 consisting of a solid state imaging device 133A combined with the prism 132 and a substrate 133B thereof. Also, between the object lens group 131 and the prism 132, there is provided a filter 134 having a desired characteristic, and further a beam limiting device (not shown) or the like are provided in addition.

A part (one or a plurality) of lens 131A constituting the object lens group 131 are movable lenses which are movable in the optical axis direction, and the remaining lenses 131B are stationary lenses. The stationary lens 131B is fixedly mounted to a lens supporting frame 135 constituting a stationary lens frame 136, and this lens supporting frame 135 is joined with the surface of the prism 132. The movable lens 131A is mounted to a movable lens frame, and this movable lens frame 136 is caused to slide along the inner surface of the lens supporting frame 135, whereby the movable lens 131A is to move in the optical axis direction between the position indicated in FIG. 4 and the position indicated in FIG. 5. This movable lens 131A is a movable member provided at the tip end of the insertion unit 3.

Figure 10:
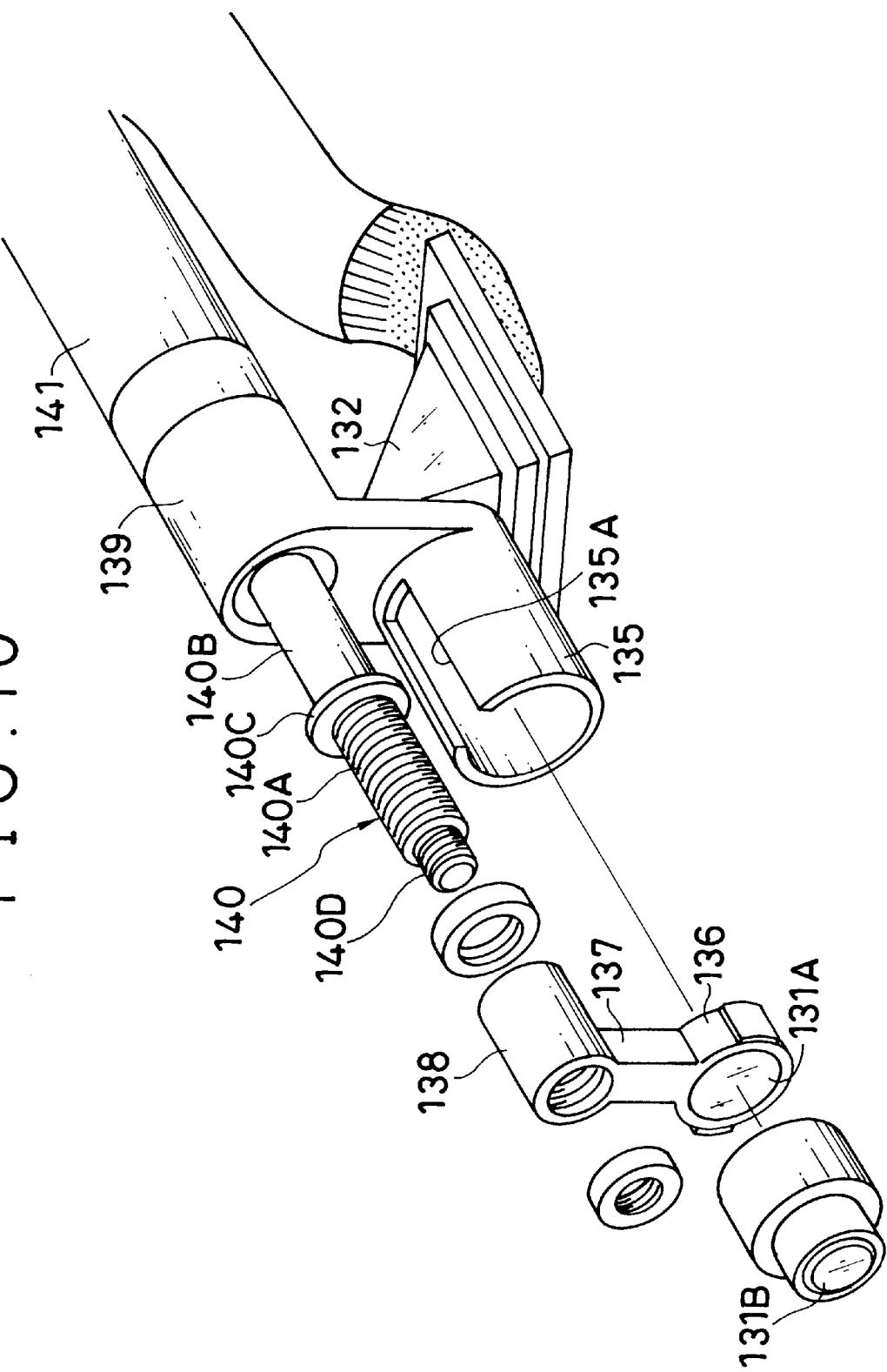
FIG. 10 is an exploded perspective view showing a lens assembly.

As shown in FIG. 10, in order to cause the optical axis of the movable lens 131A to accurately coincide with that of the stationary lens 131B, the movable lens frame 136, in which the movable lens 131A has been provided, is movable in the optical axis direction within the lens supporting frame 135, and is fixedly held in any other directions than it, that is, a direction perpendicular to the optical axis and in the falling direction.

An arm portion 137 is provided contiguous to the movable lens frame 136, and this arm portion 137 is conducted to the outside through a slit 135A provided on the lens supporting frame 135 along the optical axis direction, and contiguous to a tip end portion thereof, there is provided a nut portion 138. The dimension of the arm portion 137 in the widthwise direction is substantially the same as the groove width of the slit 135A, whereby the movement of the movable lens frame 136 in the rotating direction is regulated.

The above described configuration substantially regulates any other movement of the movable lens frame 136 than in the optical axis direction. The nut portion 138 is caused to move in a direction parallel to the optical axis along the threaded shaft 140, whereby the movable lens frame 136 is to move in the optical axis direction. The movable lens 131A has been made to be movable in the optical axis direction in order to make, variable, at least one of the observation depth, focusing multiplying factor and angle of visibility or the like. Therefore, this movable lens 131A is a movable member provided at the tip end of the insertion unit 103.

The movable lens 131A is movable by means of remote control from the body operating unit 102. For this reason, a protruding portion 135B is provided contiguous to the lens supporting frame 135, and a shaft branch portion 139, which has been formed in a substantially cylinder shape, is provided contiguous to this protruding portion 135B. The threaded shaft 140 comprises a threaded lever portion 140A and a rotating shaft portion 140B, and the rotating shaft portion 140B is inserted and fitted in an insertion hole 139A formed in the shaft branch member 139 so as to be able to freely rotate but not to move. The threaded lever portion 140A projects from the shaft branch member 139 by a predetermined length, and the nut portion 138 is threadably engaged with the protruded portion of this threaded lever portion 140A.

Reference numeral 141 denotes a control cable, which is constructed by inserting a transmission coil 143 through the flexible protective tube 142. The tip end of the transmission coil 143 is coupled to the threaded shaft 140 through a coupling member 144. This coupling member 144 has the transmission coil 143, the tip end portion of which has been inserted and fitted therein, and is configured by a cylindrical portion 144A to be fixed by soldering, brazing or the like, and the threaded lever portion 144B to be threadably inserted into the threaded shaft 140. The threaded lever portion 144B is threadably inserted into the threaded shaft 140, and is fixed with adhesive or the like. Therefore, the flexible end of the transmission coil 143 becomes the proximal end of the cylindrical portion 144A. On the other hand, the tip end of the protective tube 142 is inserted and is fitted in a connecting ring 145 threadably engaged with the proximal end of the shaft branch member 39, is fixed by means such as bonding, and on the side of the outer periphery of the protective tube 142, a clamping ring 146 is fitted in, and is fixed by using adhesive or the like. Therefore, the flexible end of the protective tube 142 is located at the position of the proximal end of the connecting ring 145 and the clamping ring 146. In this respect, if the connecting ring 145 and the clamping ring 146 differ in position of the end portion, the position of the end portion of the member located closer to the proximal end side becomes the position of the flexible end of the protective tube 142.

When the proximal end of the transmission coil 143 is rotated around the shaft within the protective tube 142, its rotating force is transmitted to the threaded shaft 140, and this threaded shaft 140 is rotated to move the nut portion 138 and the movable lens frame 136 coupled thereto. During this period of time, since the threaded shaft 140 is fixed so as not to move axially, the outside diameter of the coupling member 144 is larger than the hole diameter of the insertion hole 139A, and the rotating shaft portion 140B of the threaded shaft 140 is formed with a flange portion 140C. The coupling member 144 and the flange portion 140C abut upon the end surfaces before and after the insertion hole 139A respectively.

The control cable 141 is extended from the insertion unit 103 within the body operating unit 102, and is coupled to the rotary driving unit described in the first embodiment.

Figure 11:
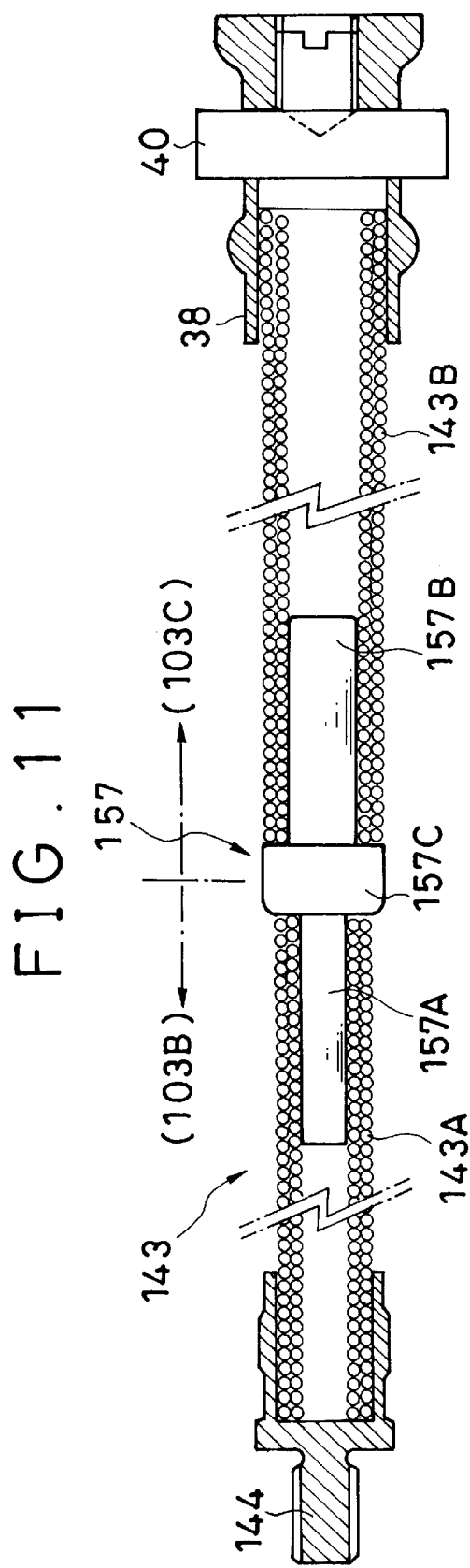
FIG. 11 is a sectional view showing a transmission coil according to a second embodiment.

As shown in FIG. 11, the transmission coil 143 has different coil diameters in a portion within the angle portion 103B, and in a portion within the soft portion 103C although the line diameter of metallic wire constituting the transmission coil 143 is the same. More specifically, between the connecting portion to the coupling member 144 to be coupled to the threaded shaft 140 and the interior of the angle portion 103B, there is a small-diameter coil portion 143A having a small coil diameter, while between the distal member 38 and the soft portion 103C, there is a large-diameter coil portion 143B having a large coil diameter. These small-diameter coil portion 143A and large-diameter coil portion 143B are coupled with each other through a joint member 157 provided at the position of a coupling portion between the angle portion 103B and the soft portion 103C.

The joint member 157 is used to couple such that the large-diameter coil portion 143B and the small-diameter coil portion 143A are integrally rotated, and a coupling side to the small-diameter coil portion 143A is a small-diameter rod portion 157A which substantially coincides with the inside diameter of this small-diameter coil portion 143A, while a coupling side to the large-diameter coil portion 143B is a large-diameter rod portion 157B which substantially coincides with the inside diameter of this large-diameter coil portion 143B. A shift portion between the small-diameter rod portion 157A and the large-diameter coil portion 143B is a flange portion 157C whose size does not exceed the outside diameter of the large-diameter coil portion 143B. The small-diameter rod portion 157A is inserted into the proximal end of the small-diameter coil portion 143A, and the large-diameter rod portion 157B is inserted into the tip end portion of the large-diameter coil portion 143B, and in such a state, they are fixed by means such as soldering respectively.

In this case, the transmission coil 143 at the coupling portion between the small-diameter coil portion 143A and the large-diameter coil portion 143B is to be made hard by a length corresponding to that of the joint portion 157 provided. As shown in FIG. 7, however, the coupling ring 158 has been provided at the coupling portion between the angle portion 103B and the soft portion 103C, and a length H along which the coupling ring 158 has been positioned becomes a hard portion. Therefore, if the length of the joint portion 157 is such a size as not to actually protrude from this coupling ring 158, the flexibility of the insertion unit 103 in the bending direction will not be particularly affected even if the transmission coil 143 becomes hard in this position.

The movable lens 131A is moved in the optical axis direction not always when the angle portion 103B has been made straight, but also the above-described movement may be performed even when this angle portion 103B has been curved. Therefore, at this time, the transmission coil 143 is to slide along the inner surface of the protective tube 142. Therefore, at least the inner surface of the protective tube 142 is made slippery, whereby the sliding resistance is restrained to a minimum, but still when the transmission coil 143 is strongly pressed against the protective tube 142, the sliding resistance may be increased to cause transmission unevenness in rotation, or to cause a locked state in a serious case. When it is abruptly curved, the protective tube 143 becomes deformed so as to become flat against its shape retention. Particularly when the angle portion 103B is curved to the maximum angle of curvature, the protective tube 142 becomes deformed most large. In this case, when the protective tube 142 is given rigidity to such a degree as not to be easily bent in order to reduce the degree of becoming flat, there arises inconvenience that the bending rigidity of the entire insertion unit 103 is increased to worsen the insertion ability.

Figure 12:
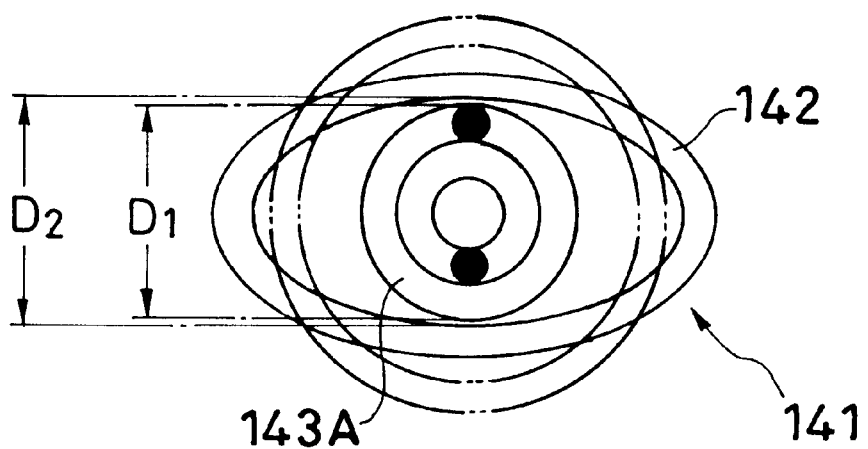
FIG. 12 is a sectional view showing states of the linear transmission member and the protective tube when the angle portion is curved.
Figure 13A:
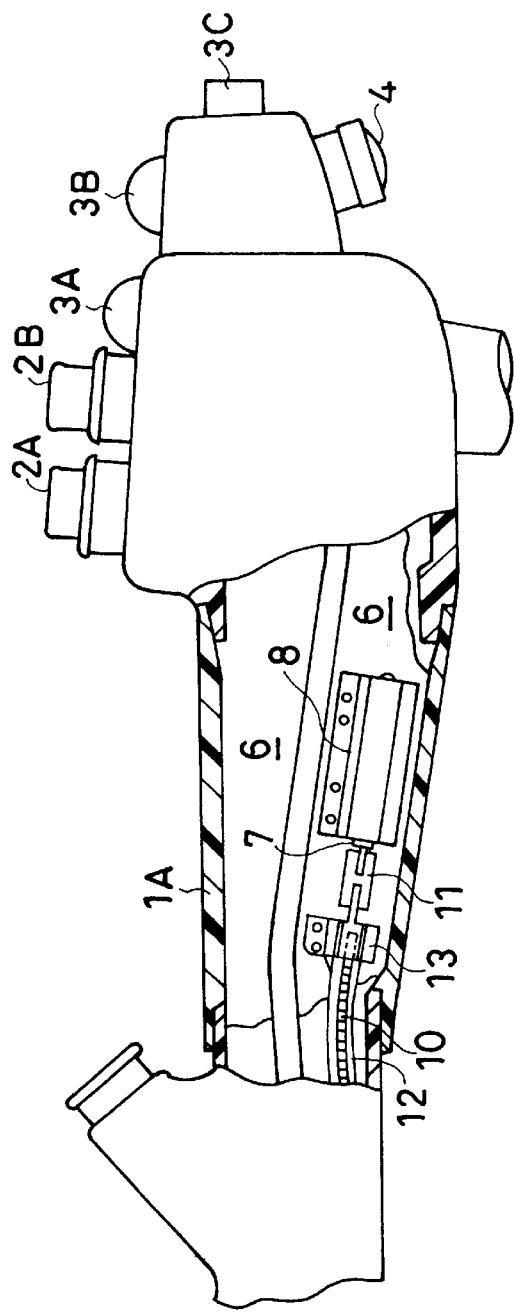
FIG. 13A is a partially exploded view showing the operating unit of the endoscope to which a mechanism for making a conventional observation distance variable has been applied.
Figure 13C:
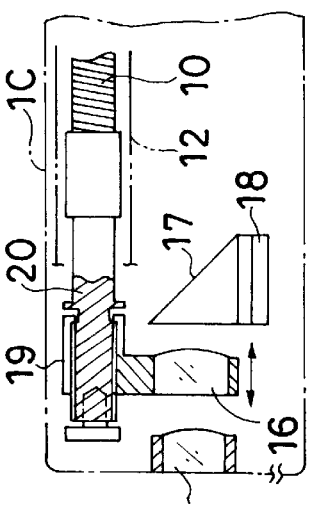
FIG. 13C is a view showing a configuration of a conventional tip portion of the endoscope.
Figure 13B:
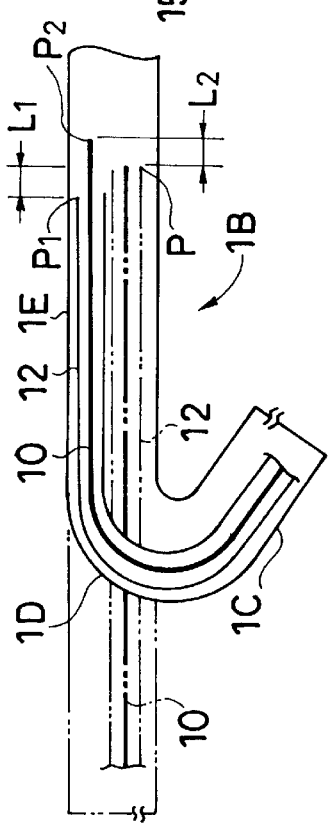
FIG. 13B is a view showing a configuration of a conventional insertion unit of the endoscope.

From the foregoing, as shown in FIG. 12, in a state in which no bending force is exerted on the protective tube 142, it is held in a circular shape as indicated by an imaginary line, and when the angle portion 103B is curved to the maximum angle of curvature, it is assumed that it becomes deformed so as to become flat as indicated by a solid line in FIG. 12. Even if it becomes most flat, space to such a degree that any movement within the protective tube 142 of the transmission coil 143 is not restrained as far as possible is secured. Therefore, assuming $D_1$ of FIG. 12 to be an outside diameter of the small-diameter coil portion 143A of the transmission coil 143, and $D_2$ to be a dimension of a minor axis when the protective tube 142 has been most flattened, $D_2$ is made equal to $D_1$ or to be a larger dimension. Thereby, even when the angle portion 103B is curved to the maximum angle of curvature, the transmission coil 143 is caused to have space in which the transmission coil 143 is capable of still moving within the section of the protective tube 142. In other words, however the protective tube 142 maybe flattened, a sufficient difference in diameter is allowed between the inside diameter of the protective tube 142 and the outside diameter of the transmission coil 143 so as to secure at least larger space than the outside diameter of the transmission coil 143. In the transmission coil 143, a portion located within the angle portion 103B has been set to the small-diameter coil portion 143A for this reason. Therefore, the smaller the outside diameter of the small-diameter coil portion 143A is, the transmission coil 143 can be smoothly rotated with a light load even when the angle portion 103B has been curved.

In the soft portion 103C, its curvature is gentle even if it is curved along the insertion course, and therefore, in a state in which it is inserted into a body cavity, there is no possibility that the protective tube 142 becomes deformed so as to be flattened within this soft portion 103C, and therefore, it is not necessary to make a difference in diameter between the outside diameter of the transmission coil 143 and the inside diameter of the protective tube 142 much large. For this reason, of the transmission coils 143, a portion located within the soft portion 103C is set to the large-diameter coil portion 143B, whereby the difference in diameter with the inside diameter of the protective tube 142 is made into a minimum size required. Since the soft portion 103C has a much longer size than the angle portion 103B, the difference in diameter between the transmission coil 143 and the protective tube 142 in this portion is made small, whereby the fluctuation width in the length of conduction of the transmission coil 143 from the protective tube 142 can be restricted to a minimum when the insertion unit 103 is narrow.

According to the second embodiment, there is exhibited an effect on driving a movable member provided at the tip end of the insertion unit that the frictional resistance between the transmission coil and the protective tube can be restricted to a minimum.

In this respect, in each embodiment described above, the description has been made of a member for moving a part of an object lens group constituting an objective optical system of an electronic endoscope in the optical axis direction, but the movable member provided at the endoscope and the tip end portion of the insertion unit thereof is not limited thereto. Also, the linear transmission member has been driven by a motor, but the structure can be arranged so as to drive by manual operation or the like.

What is claimed is:

1. A linear transmission member driving unit for an endoscope, comprising:

a linear transmission member which performs a rotary motion in order to drive an object;

a protective tube which rotationally envelops said linear transmission member;

a motor, to which said linear transmission member is shaft-connected;

a chassis to which said motor is fixed; and a mobile type linear transmission member shaft coupling mechanism, which couples a shaft of said motor fixed to said chassis to an end portion of said linear transmission member, and to which said linear transmission member is mounted so as to be able to move in a direction of a rotating shaft of said motor.

2. The linear transmission member driving unit for an endoscope according to claim 1, wherein said mobile type linear transmission member shaft coupling mechanism is configured by a cylindrical member coupled and fixed to said motor shaft, and comprises:

a shaft connecting member in which a sliding guide hole having a predetermined length in the direction of said rotating shaft is formed; and a distal member of said linear transmission member, which is disposed so as to move within a cylinder of said shaft connecting member, and, in which there is provided a pin for engaging with said sliding guide hole to slide, wherein a pin of said distal member is caused to be engaged with said sliding guide hole, whereby it is made possible to transmit rotation of said motor to said linear transmission member and to move said linear transmission member concerned in the direction of said rotating shaft by a predetermined amount.

3. The linear transmission member driving unit for an endoscope according to claim 1, wherein said motor and said mobile type linear transmission member shaft coupling mechanism are disposed in space on a side of an angle operating knob mechanism being mounted, partitioned by said chassis within an operating unit, and said motor and said protective tube are caused to be mounted to said chassis concerned by the use of an integrally formed holding member.

4. The linear transmission member driving unit for an endoscope according to claim 1, wherein as said chassis, a plurality of sheets of plates are superposedly disposed, and the rotating shaft for said angle operating knob and said holding member are caused to be mounted onto different plates respectively.

5. The linear transmission member driving unit for an endoscope according to claim 1, wherein lubricating coat is applied to a sliding member of said mobile type shaft coupling mechanism.

6. The linear transmission member driving unit for an endoscope according to claim 2, wherein on an outer periphery of said distal member, there are formed protruding portions in contact with an inner wall of said shaft connecting member at two places where said pin is sandwiched therebetween such that said linear transmission member is caused to move by sliding of said protruding portions within said shaft connecting member concerned.

7. A linear transmission member driving unit for an endoscope, comprising:
   a movable member disposed on the side of the tip end of an insertion unit having an angle portion and a soft portion;
   a transmission coil, which is a linear transmission member for transmitting the rotary driving force of said motor to said movable member, comprising wire spirally wound; and
   a flexible protective tube which rotationally envelops said transmission coil,
   wherein said transmission coil, whose wire diameters are actually the same, comprises two coil portions having different outside diameters, has a small-diameter coil portion having smaller outside diameter within said angle portion, and a large-diameter coil portion having a larger outside diameter within said soft portion, these both coil portions being coupled by a coupling member so as to be able to integrally rotate at a connecting position between said angle portion and said soft portion or in the vicinity thereof.

8. The linear transmission member driving unit for an endoscope according to claim 7, wherein an outside diameter of said small-diameter coil portion is set so as to be smaller than a size in a direction of an end shaft when said angle portion goes into a maximum curved state and said protective tube becomes deformed so as to be flattened.

9. The linear transmission member driving unit for an endoscope according to claim 7, wherein said movable member is a movable lens among an object lens group provided at said tip hard portion.

10. The linear transmission member driving unit for an endoscope according to claim 7, wherein said transmission coil comprises bonded coil, and said bonded coil is configured by a double coil comprising coils wound in opposite directions to each other.

* * * * *